(12) United States Patent
Vartiainen

(10) Patent No.: US 6,399,854 B1
(45) Date of Patent: Jun. 4, 2002

(54) ABSORBENT ARTICLE IN AN ABSORBENT STRUCTURE

(75) Inventor: Kent Vartiainen, Lerum (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/695,218

(22) Filed: Oct. 25, 2000

Related U.S. Application Data

(63) Continuation of application No. PCT/SE99/00738, filed on May 4, 1999.

(30) Foreign Application Priority Data

May 12, 1998 (SE) .............................................. 9801694

(51) Int. Cl.[7] .................................................. A61F 13/15
(52) U.S. Cl. .................. 604/367; 264/45.3; 428/317.1; 428/317.7; 428/315.5; 604/369
(58) Field of Search ................................ 604/369, 368, 604/367; 264/45.3, 46.8, 45.2, 51; 428/315.5, 317.9, 317.1, 317.7

(56) References Cited

U.S. PATENT DOCUMENTS

| | | | |
|---|---|---|---|
| 3,598,742 A | | 8/1971 | Summit et al. |
| 4,676,784 A | * | 6/1987 | Erdman et al. .............. 604/368 |
| 5,707,571 A | * | 1/1998 | Reedy ........................ 264/45.3 |
| 5,763,067 A | * | 6/1998 | Bruggemann et al. ... 428/317.9 |
| 5,817,081 A | * | 10/1998 | LaVon et al. ................ 604/378 |
| 5,851,648 A | * | 12/1998 | Stone et al. .............. 428/304.4 |
| 5,863,958 A | * | 1/1999 | Dyer et al. .................... 521/63 |
| 5,899,893 A | * | 5/1999 | Dyer et al. ................. 604/358 |
| 6,015,935 A | * | 1/2000 | LaVon et al. ................ 604/378 |
| 6,017,417 A | * | 1/2000 | Wendt et al. ................ 162/109 |

FOREIGN PATENT DOCUMENTS

| | | |
|---|---|---|
| EP | 160572 | 11/1985 |
| EP | 219969 | 4/1987 |
| EP | 301753 | 2/1989 |
| GB | 2259441 | 3/1993 |
| TW | 347321 | 12/1998 |
| WO | 9621409 | 7/1996 |

* cited by examiner

Primary Examiner—John G. Weiss
Assistant Examiner—Jacqueline F Stephens
(74) Attorney, Agent, or Firm—Burns, Doane, Swecker & Mathis, L.L.P.

(57) ABSTRACT

An absorbent structure in an absorbent article such as a diaper, incontinence guard, sanitary napkin, dressing or the like. The structure being useful for the absorption of bodily fluids or discharges, e.g., urine and blood. The absorbent structure containing a carrier material in the form of an open-cell foam having hydrophilic fibers deposited within the pore structure of the open-cell foam.

2 Claims, 3 Drawing Sheets

ABSORBENT ARTICLE IN AN ABSORBENT STRUCTURE

This application is a continuation of application Ser. No. PCT/SE99/00738 filed May 4, 1999.

TECHNICAL FIELD

The present invention refers to an absorbent structure in an absorbent article such as a diaper, pant diaper, incontinence guard, sanitary napkin, dressing and the like.

BACKGROUND OF THE INVENTION

Absorbent articles of the above mentioned kind are intended for the absorption of body liquids such as urine and blood. They usually have a liquid pervious topsheet, which during use is intended to be facing the wearer's body and which for example consists of a nonwoven material of spunbond type. Further they have a liquid impervious backsheet, e g a plastic film or a hydrophobic nonwoven material, and an absorbent structure arranged between the liquid pervious topsheet and the liquid impervious backsheet. The absorbent structure may comprise more than one layer such as liquid acquisition layer, storage layer and distribution layer.

As an acquisition layer there is normally used a porous material with a high momentaneous liquid receiving capacity. Example of such materials are cellulosic fluff pulp of thermomechanic or chemothermomechanic (CTMP) type, chemically stiffened cellulosic fibers, fibrous waddings, carded fibrous webs, porous foam materials etc.

As a storage layer there is normally used cellulosic fluff pulp mixed with so called superabsorbents, i e crosslinked polymers with capacity to absorb body liquids several times their own weight (10 times or more). It is also possible to use an absorbent foam material as a storage layer. As a distribution layer there can be used cellulosic fluff pulp, tissue; layer, foam, synthetic fibers and the like having a high liquid distribution capability. It is also possible to combine two or more of the functions, acquisition, storage and distribution in the same layer.

In order to for example save space during storage and transports it is common to compress the absorbent articles strongly, which for materials with a low resiliency such as cellulosic fluff pulp, especially of chemical type, means that they maintain a high density also after they have been taken out from their package. This can in turn influence especially the liquid acquisition capacity negatively. It is therefore common to use a resilient material which can spring back as a liquid acquisition layer on top of a compressed absorbent core of cellulosic fluff pulp and superabsorbent.

EP-A-0 301 753 discloses an absorbent structure in the form of an open-cell foam material, which has been impregnated with a superabsorbent material. The superabsorbent material is retained in the foam by a binder. The preparation of the foam is made by dispersing the superabsorbent material in a solvent, after which the foam is impregnated with the dispersion and then the solvent is evaporated.

EP-A-0 160 572 discloses an absorbent structure comprising a carrier material applied in a fibrous structure. The carrier material can e g have a net-like structure and comprises a hydrophilic porous material, e g fibers or foam.

OBJECT AND MOST IMPORTANT FEATURES OF THE INVENTION

The object of the present invention is to provide an absorbent structure comprising a material with high spring back in dry as well as in wet condition and which besides has a high absorbent capacity. This has been achieved by the fact that the absorbent structure comprises a carrier material in the form of an open-cell foam containing hydrophilic fibers in its pore structure.

The hydrophilic fibers according to one embodiment at least partly are cellulosic fibers.

The foam material can in its pore structure further contain superabsorbent material.

The foam preferably has a relatively large pore size of no more than 15 and more preferably no more tan 10 pores per linear inch (no more than 6 and preferably no more than 4 pores per linear cm).

According to one embodiment the absorbent structure has a three-dimensional shape provided by heating and shaping of the foam material.

The invention firer refers to a method for manufacturing an absorbent structure in an absorbent article as above, at which hydrophilic fibers by means of a vacuum is sucked into an open-cell foam material.

Moreover it refers to an absorbent article such as a diaper, pant diaper, incontinence guard, sanitary napkin, bed protection, dressing and the like, which comprises an absorbent structure according to the invention. The absorbent structure can be arranged as a liquid acquisition layer, as a combined liquid acquisition- and storage layer or as a combined topsheet and liquid acquisition layer.

DESCRIPTION OF THE DRAWINGS

The invention will in the following be closer described with reference to an embodiment shown in the accompanying drawings.

DESCRIPTION OF EMBODIMENTS

The absorbent structure 10 according to the invention comprises a carrier material 11 in the form of an open-cell foam, preferably a so called reticulated foam, which means a foam having a three-dimensional structure defining separate cells, in which the main part or all cell wall membranes are broken so that only a skeleton of the three-dimensional structure remains. The carrier material contains in its pore structure hydrophilic fibers 12. The pore size of the foam must be relatively large, preferably no more 15 and more preferably no more than 10 pores per linear inch (ppi) (no more than 6 and preferably no more than 4 pores per linear cm), which corresponds to a mean pore size of at least 2.5 mm in diameter. The foam cam be of an optional polymeric material with the capability to form a three-dimensional structure of the above kind, such as a polyurethane foam. The foam should preferably be hydrophilic, but may also be hydrophobic.

The hydrophilic fibers 12 can be cellulosic fibers, regenerated cellulosic fibers such as rayon, viscose, hydrophilic synthetic fibers or natural fibers of optional kind. Preferably at least a part of the fibers 12 are cellulosic fluff pulp such as chemical pulp, thermomechanical pulp, chemothermomechanical pulp (CTMP) or pulp of chemically stiffened and/or crosslinked cellulosic fibers. Since the fibers are contained in the foam structure also short fibers can be used, which otherwise can be difficult to use in absorbent articles, since they lead to a low strength of the fiber structure, which means that his easily bursts or crumbles. The foam structure contributes to give the required tensile strength to the material.

The weight relationship between fibers and foam can vary within wide limits but the amount of fibers should be at least 10 and preferably at least 25% by weight calculated on the total weight of the foam and fibers. The amount of fibers can amount to many times the weight of the foam.

Figure 2:
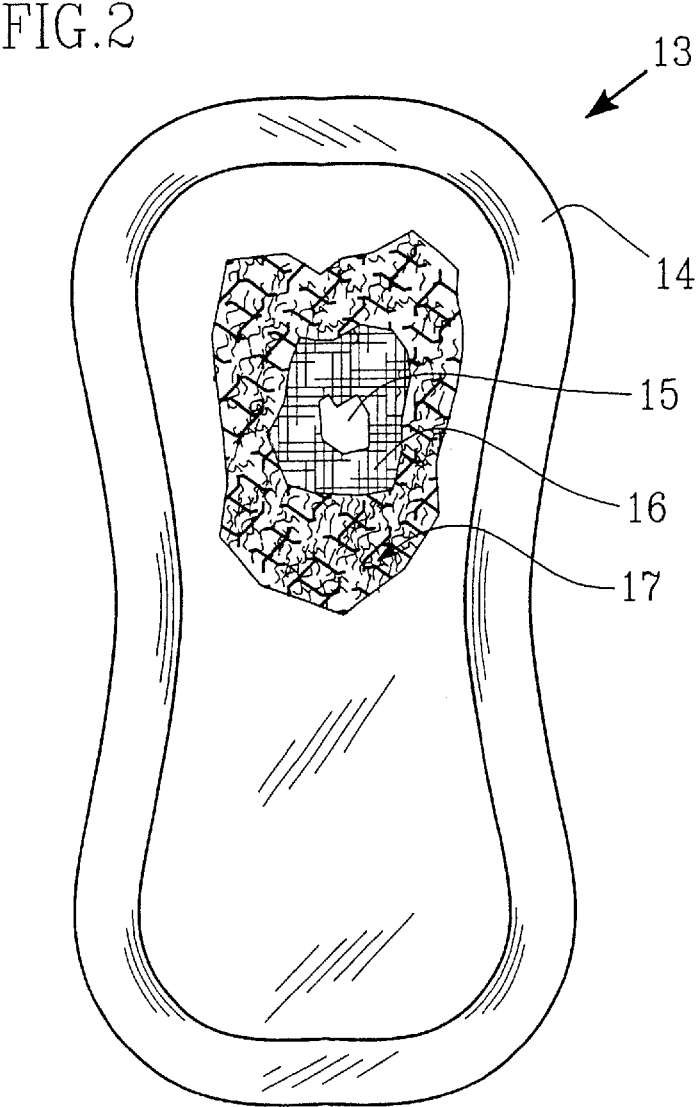
FIG. 2 is a plan view of an absorbent article in the form of an incontinence guard.

The absorbent structure is intended to be used in an absorbent article such as a diaper, pant diaper, incontinence guard, sanitary napkin, bed protection, dressing and the like. In FIG. 2 there is disclosed an embodiment of an incontinence guard 13, which comprises a liquid pervious topsheet 14, a liquid impervious backsheet 15 and an absorbent layer 16 enclosed. A porous and resilient liquid acquisition layer 17 is further arranged between the liquid pervious topsheet 14 and the absorbent layer 16.

The liquid pervious topsheet 14 can consist of a nonwoven material, e g a spunbond material of synthetic filaments, a meltblown material, a thermobonded material, a bonded carded fibrous material or a perforated plastic film. The liquid impervious backsheet 15 usually consists of a plastic film, a nonwoven material coated with a liquid tight material or a hydrophobic nonwoven material which resists liquid penetration.

The topsheet 14 and the backsheet 15 have a somewhat larger extension in the plane than the absorbent layer 16 and extend outside the edges thereof. The layers 14 and 15 are interconnected within their projecting portions, e g by gluing or welding with heat or ultrasonic.

The absorbent layer 16 can be of any conventional kind Examples of commonly used absorption materials are cellulosic fibers e g in the form of cellulosic fluff pulp, tissue layers, highly absorbent polymers (so called superabsorbents), absorbent foam materials, absorbent nonwoven materials and the like. It is common to combine cellulosic fluff pulp with superabsorbents in an absorbent layer. It is also common to have absorbent bodies comprising layers with different properties wit respect to liquid acquisition, liquid distribution and liquid storage capacity. This is wellknown for the person skilled in the art and therefore needs not to be described in detail. The absorbent bodies that are common in e g baby diapers and incontinence guards often comprise a compressed mixed or layered structure of cellulosic fluff pulp and superabsorbent particles.

An incontinence guard of the kind shown in FIG. 2 is at first hand intended to be used by persons having relatively light incontinence and are easily worn in ordinary underpants. Attachment means in the form of areas of selfadhesive glue can be arranged on the outside of the liquid impervious backsheet 15. Other types of attachment means such as hook and loop, snap fasteners, girdles, special tightly fitting underpants and the like may of course also be used.

It should be noted that the incontinence guard shown in the drawings and described above is a non-limiting example of an absorbent article. Thus the shape and design of the article can be varied. The absorbent article may also be a diaper, a pant diaper, a sanitary napkin, a bed protection, a dressing or the like.

Between the liquid pervious layer 14 and the absorbent layer 16 there is arranged a porous and resilient acquisition layer 17 with the capability to quickly receive large amounts of liquid and to distribute liquid and temporarily store it before it is absorbed by the underlying absorbent body 16. This capability should be essentially maintained also after wetting of the material. The acquisition layer 17 can either cover the entire absorbent layer 16 or only the central parts thereof.

Figure 1:
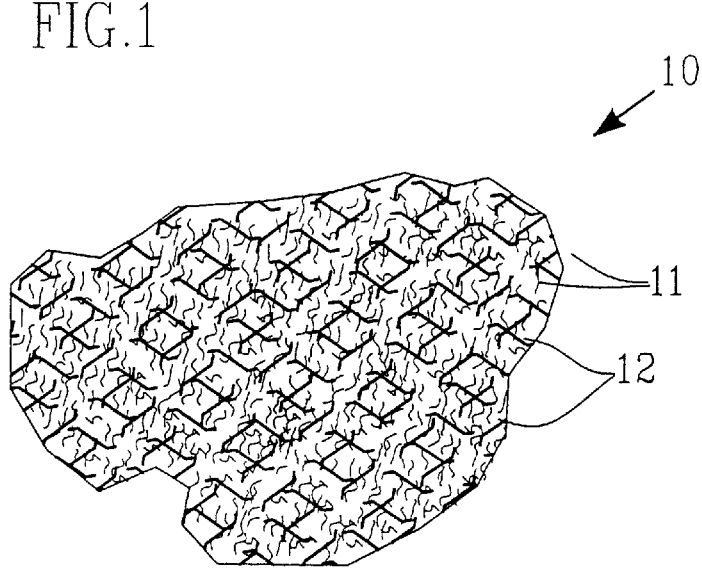
FIG. 1 shows on an enlarged scale a schematic section through a portion of an absorbent structure according to the invention.

According to the invention the acquisition layer 17 consists of an absorbent structure 10 according to FIG. 1, i e a reticulated foam 11 containing hydrophilic fibers 12.

Figure 3:
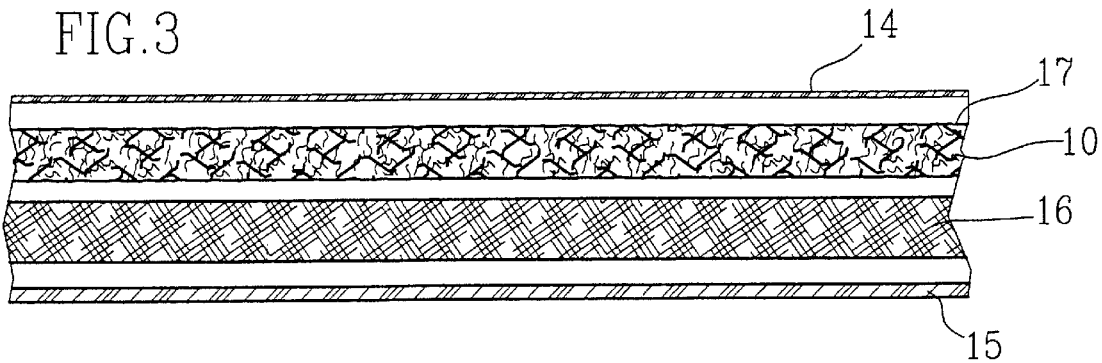
FIGS. 3–5 show schematic exploded sections trough absorbent articles according to some different embodiments.

In the embodiment shown in FIG. 2 the absorbent structure according to the invention is used as a liquid acquisition layer under a liquid pervious topsheet 14. This is also shown in FIG. 3 which is a schematic exploded view through an absorbent article comprising a liquid pervious topsheet 14, a liquid acquisition layer 17, an absorbent layer 16 and a liquid impervious backsheet 15.

The liquid acquisition layer 17 consists of an absorbent structure according to the invention, i e a reticulated foam containing hydrophilic fibers, while the absorbent layer 16 can be of optional type, such as cellulose fluff pulp having superabsorbent mixed therewith, an absorbent foam material etc. There could possibly also be arranged a special liquid distribution layer between the acquisition- and the absorbent layer 17 and 16 or between the absorbent layer 16 and the backsheet 14. Alternatively the acquisition or the absorbent layer 17 and 16 respectively functions also as a liquid distribution layer.

The reticulated foam with fibers therein functioning as an acquisition layer can also contain a certain amount of superabsorbent material for absorbing any liquid that may remain in the pore system of the foam, so that rewetting against the wearer is avoided and the surface facing the wearer remains dry. By the fact that the superabsorbent is carried within the resilient foam structure 11 it is also possible to use superabsorbent that are pressure sensitive, i e which have a low absorption capacity under load, and which otherwise would be unsuitable to use in absorbent articles which are exerted to pressure from the wearer.

The stiff resilient foam structure 11 does not collapse when it is wet but will maintain its open pore system, which gives it a high liquid acquisition capacity, i e large amounts of liquid can be received during a short period of time. By the fact that the underlying absorbent layer 16 has a finer capillary system there will be a more active liquid transport from the acquisition layer 17 to the absorbent layer 16, since the capillary forces act to transport liquid from larger to smaller capillaries. Due to the capillary difference rewet of liquid that has already been absorbed by the absorbent layer 16 is counteracted.

Figure 4:
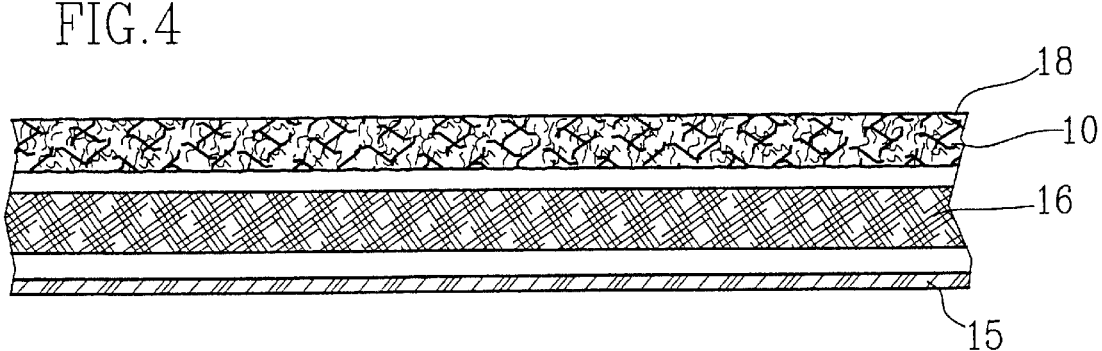

In FIG. 4 it is shown an alternative embodiment where the absorbent structure 10 according to the invention has been used as a combined liquid pervious topsheet and acquisition layer 18. Since the pulp fibers have penetrated into the reticulated foam structure the structure obtains a softness, which makes it possible to use it directly against the skin of the user.

Figure 5:
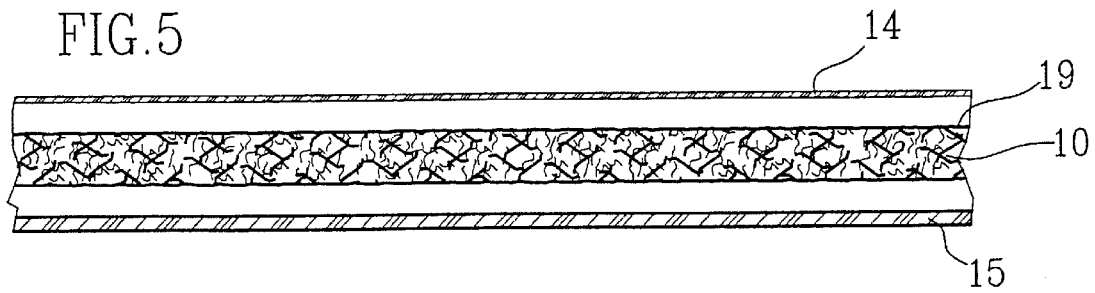

In FIG. 5 it is shown an embodiment where the absorbent structure 10 according to the invention has been used as a combined acquisition and absorbent layer 19. It can in this case be suitable to include a superabsorbent material, which has a high liquid storage capacity, into the reticulated foam structure. The layer 19 thus has a good liquid acquisition capacity as well as a high liquid storage capacity and fulfills the function of an acquisition layer as well as an absorbent/storage layer. As mentioned above pressure sensitive superabsorbents may also be used, since they are supported by the resilient foam structure, which takes up the main part of the pressure loads that may occur.

Figure 6:
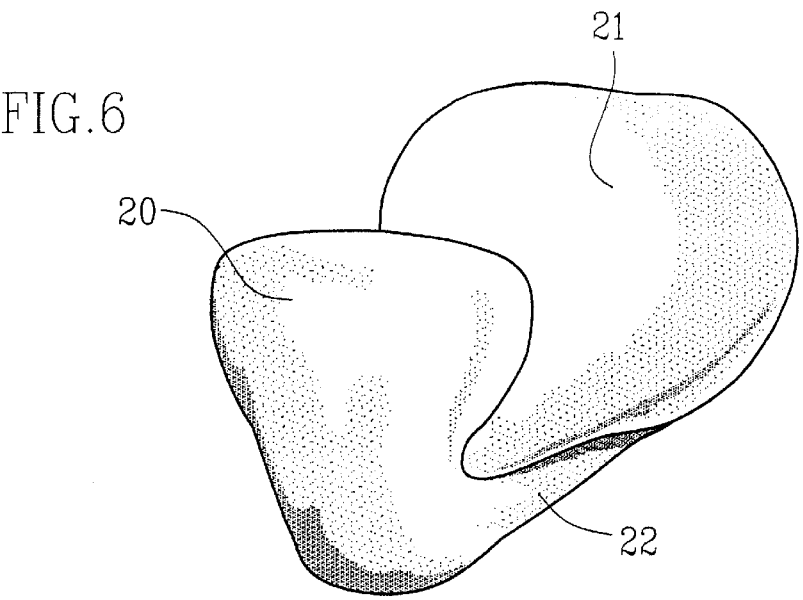
FIG. 6 shows an example of a three-dimensionally shaped absorbent article.

The absorbent structure 10 according to the invention can be three-dimensionally shaped by heating the foam structure, after which a shaping thereof may occur. The shaping can be performed either before or after the addition of fibers to the foam structure. The structure can be given a optional shape, such as bowl shape or layer shape. In FIG. 6 there is shown a non-limiting example of a three-dimensionally shaped product, e g an incontinence guard or sanitary napkin. The product has an upwardly directed front portion 20 and a correspondingly upwardly directed broader back portion 21 and a bowl-shaped crotch portion 22 arranged therebetween.

Figure 7:
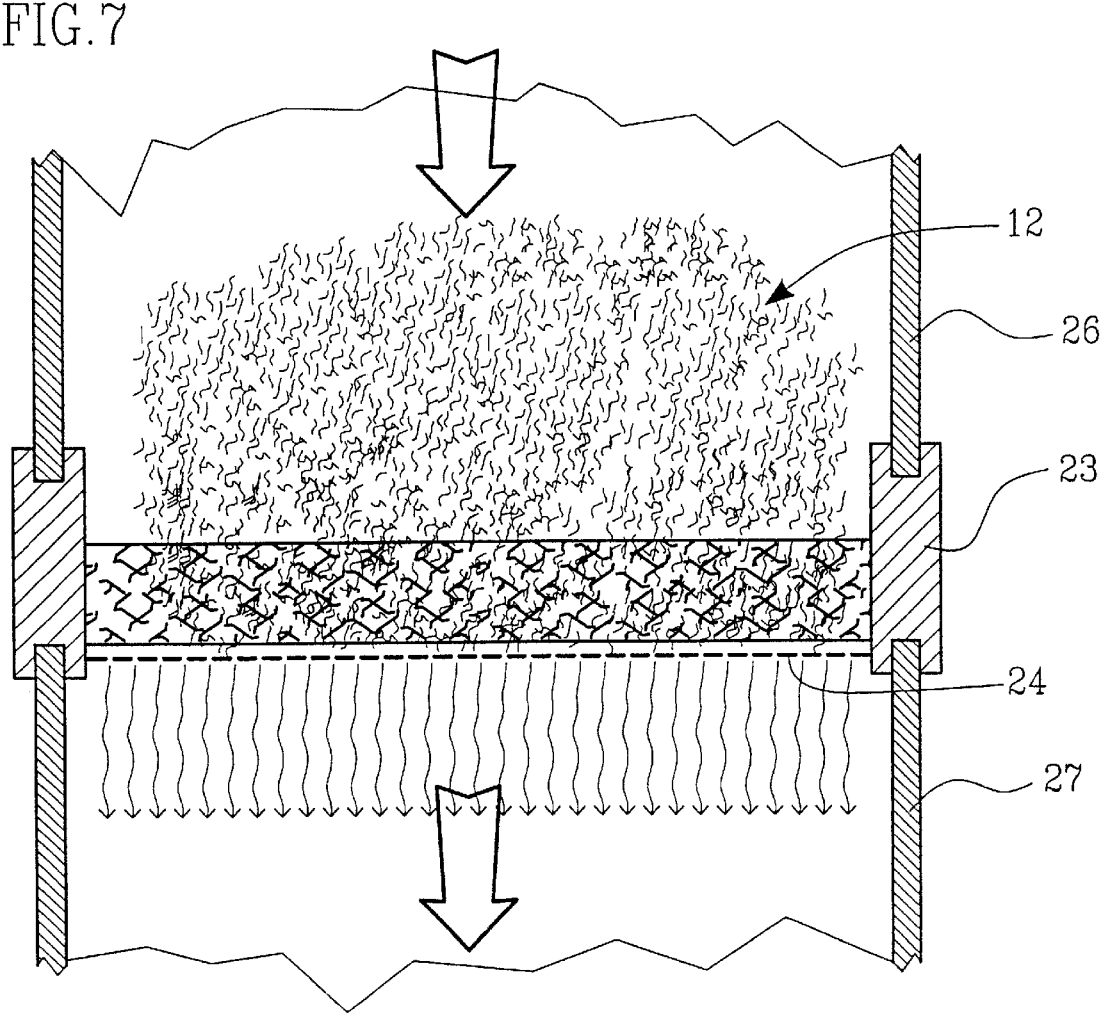
FIG. 7 illustrates schematically a method for producing the absorbent structure according to the invention.

In FIG. 7 there is schematically shown a cross section through a part of a device for making an absorbent structure according to the invention. The device comprises a mould having side walls 23 and an air pervious bottom 24. Above the mould there is arranged a chamber 26, e g a mat forming hood, which is connected to a supply conduit for air borne fibers. Under the mould there is a vacuum box 27. A reticulated foam structure 10 is placed on the air pervious bottom 24 of the mould and fibers 11 are sucked into the foam structure by the vacuum in the vacuum box. In order to suck the fibers effectively into the foam structure it is important that they hit it straightly from above as is shown in the figure.

According to an embodiment the foam structure can be stretched in one direction in connection with that the fibers are sucked into the material, which makes it easier for the fibers to penetrate into the material. This stretching of the material is stopped after the fibers have been added, at which the material reverts to its original dimension.

Below some tests are disclosed which have been made with respect to the absorbent capacity of an absorbent structure according to the invention.

The capacity for reticulated foam with pulp fibers

Sample bodies consisting of 100% chemical cellulose pulp (=Ref.) and of a reticulated foam of polyurethane 10 ppi (pores per linear inch) (=4 pores per linear cm) with pulp fibers integrated therein (43 weight % foam+57 weight % pulp fibers) (=Test) respectively were measured with respect to dry bulk, wet bulk and absorption capacity. The following results were obtained.

|  | Dry bulk ($cm^3/g$) | Wet bulk ($cm^3/g$) | Abs. capacity (g/g) |
|---|---|---|---|
| Ref. (pulp) | 21 | 10 | 12 |
| Test: (foam + pulp) | 19 | 14 | 12 |

As can be seen the reduction of bulk for the test body was considerably lower than for the reference body, which means that the test body is collapsing much less, i e the structure is maintained considerably better in wet condition. This gives a good liquid acquisition also after wetting.

Besides the capacity is the same for the reference as for the test body, but since the reticulated foam per se has the capacity 0 g/g the weight thereof can be disregarded and one then obtains an effective "pulp capacity" corresponding to 21 g/g, i e the absorbent capacity of the pulp fibers are utilized considerably better.

What is claimed is:

1. A method of making an absorbent structure in an absorbent article, the absorbent structure comprising a carrier material in the form of an open-cell foam porous structure and hydrophilic fibers within the porous structure, wherein the hydrophilic fibers are vacuum sucked into an open-cell foam material.

2. A method of making an absorbent structure in an absorbent article, the absorbent structure comprising a carrier material in the form of an open-cell foam porous structure and hydrophilic fibers within the porous structure, wherein the hydrophilic fibers are vacuum sucked into an open-cell foam material, and wherein the foam material is stretched in connection with sucking the fibers into material.

* * * * *